United States Patent [19]

Meginniss, III

[11] 4,119,113
[45] Oct. 10, 1978

[54] DOUBLE-ACTION PROPORTIONING PUMP

[75] Inventor: Stephen Mason Meginniss, III, St. Petersburg, Fla.

[73] Assignee: Extracorporeal Medical Systems, Inc., Wilmington, Del.

[21] Appl. No.: 547,625

[22] Filed: Feb. 6, 1975

[51] Int. Cl.$^2$ .................. A61M 16/00; G05D 11/02
[52] U.S. Cl. .................................. 137/99; 210/321 B; 210/416 M; 417/397; 417/404
[58] Field of Search .................. 210/22, 321 K, 96 M, 210/416 M; 137/99, 93, 101.21; 417/404, 397; 91/275; 251/65; 128/273

[56] References Cited

U.S. PATENT DOCUMENTS

| | | | |
|---|---|---|---|
| 2,427,429 | 9/1947 | Waite et al. | 225/21 |
| 2,755,966 | 7/1956 | Lindars | 91/275 X |
| 2,951,745 | 9/1960 | Sweet et al. | 417/397 X |
| 2,986,898 | 6/1961 | Wood, Jr. | 417/404 X |
| 3,174,409 | 3/1965 | Hill | 91/306 |
| 3,216,627 | 11/1965 | Best et al. | 62/193 |
| 3,406,826 | 10/1968 | Willock | 210/87 |
| 3,441,136 | 4/1969 | Serfass et al. | 210/321 X |
| 3,508,656 | 4/1970 | Serfass et al. | 210/90 |
| 3,530,873 | 9/1970 | Arp et al. | 137/101.21 X |
| 3,598,727 | 8/1971 | Willock | 210/22 |
| 3,700,360 | 10/1972 | Shaddock | 417/404 |

OTHER PUBLICATIONS

Catalog M—18 of Haskel Eng. & Supply Co., 4/73.
Catalog M—28 of Haskel Eng. & Supply Co., 9/75.
Sheets 2 and 3 of Revision F–1073 of Haskel Bulletin, 1966.
A bulletin of Seattle Artificial Kidney Supply Co., 1972, p. 6590–b.
A bulletin of the Johnson Pump Co., (Bulletin M—12).
"Human Factors in the Design of Artificial Kidney Machines", a paper presented 11/73 before Amer. Soc. of Mech. Engs.

Primary Examiner—Frank A. Spear, Jr.
Attorney, Agent, or Firm—Woodcock, Washburn, Kurtz & Mackiewicz

[57] ABSTRACT

In a blood dialysis system a proportioning pump accurately mixes precise quantities of water and concentrate. A double-acting piston assembly is disposed in a stepped cylinder which has proximity sensing switches at both ends thereof. These are operated as the piston assembly reaches the end of its stroke in each direction. The switches alternate a bistable solenoid valve system which directs pressurized water to opposite sides of a large central piston, thus causing the piston assembly to reciprocate. Small pistons, attached on opposite sides of the large piston, move in small pump chambers, with check valves. The small pistons pump concentrate in a precise ratio to the volume of water driving the large piston.

5 Claims, 5 Drawing Figures

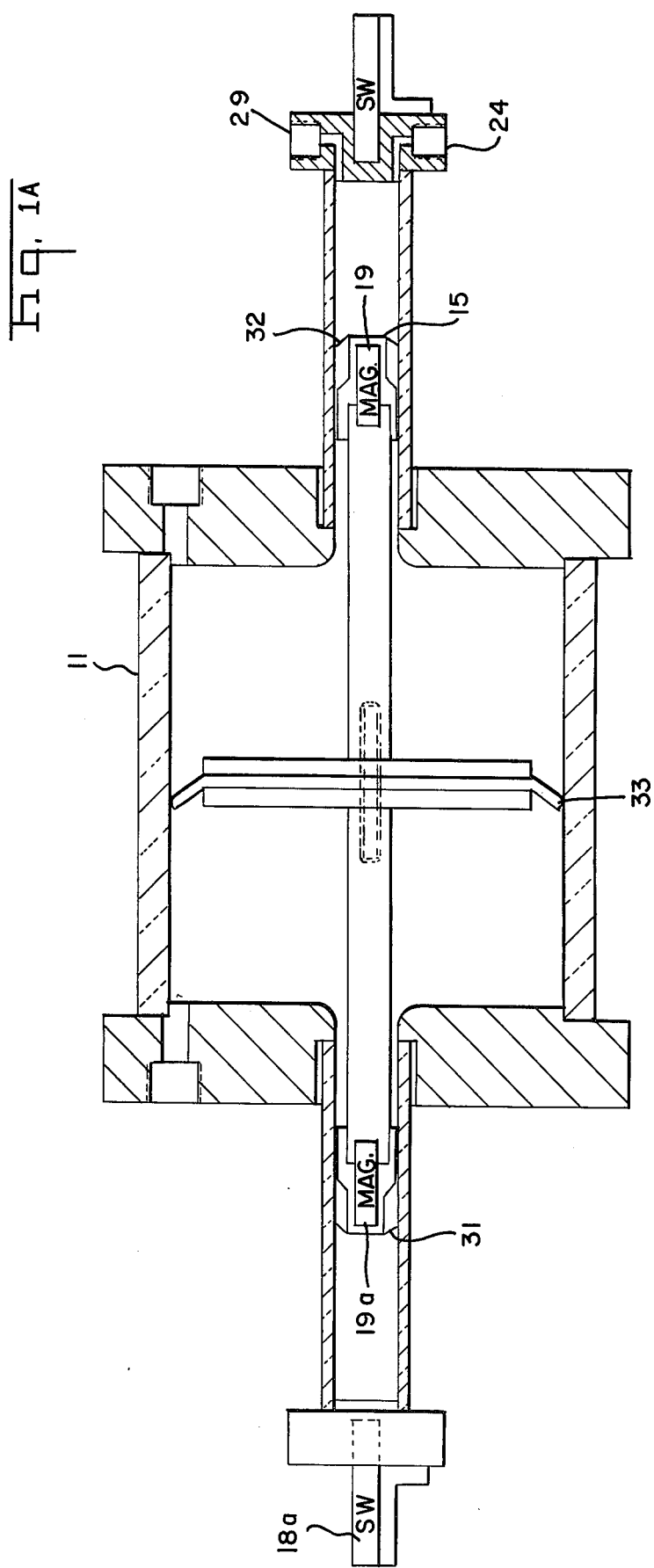

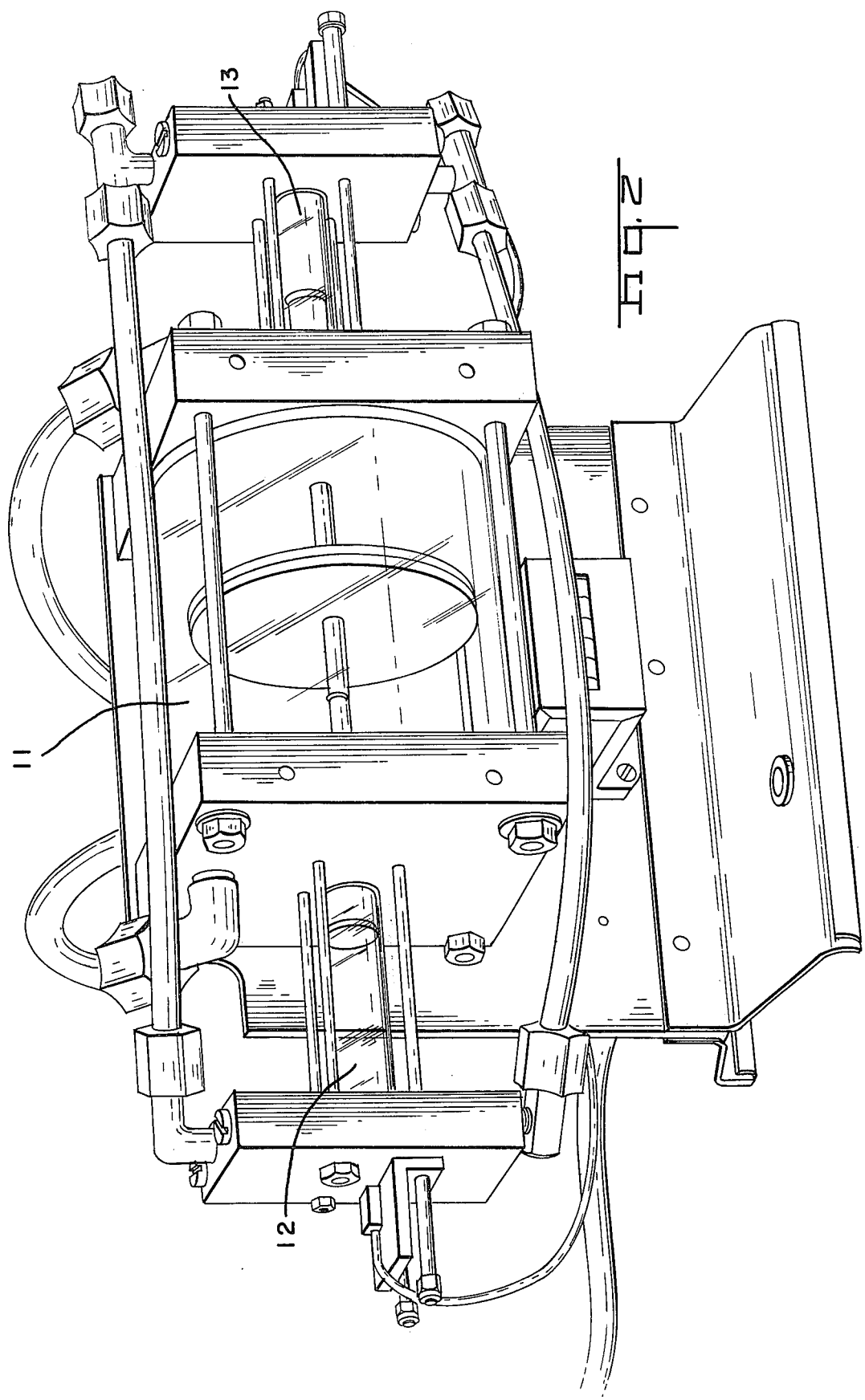

DOUBLE-ACTION PROPORTIONING PUMP

BACKGROUND OF THE INVENTION

This invention relates to an improved proportioning pump and more particularly to such a pump which is used in a blood dialysis system.

The proportioning of water with dialysate concentrate with a long-term steady state accuracy requires a highly accurate proportioning device. Those proportioning techniques which are dependent on a minimal number of physical properties remaining constant are inherently more stable and capable of higher accuracy. Physical properties which can vary include water and concentrate density, viscosity, bubbles of air, flow coefficients of orifices, constant fluid leakage characteristics and so on.

One type of proportioning pump which has been successfully used includes motor driven positive displacement cylinders. An example of such a commercially available pump is the mRoy proportioning pump available from the Milton Roy Company, St. Petersburg, Florida. U.S. Pat. No. 3,441,136 — Serfass shows the use of such a pump in a blood dialysis system.

Feedback controlled proportioning systems automatically attempt to adjust their control action to offset one or more changing physical properties. U.S. Pat. No. 3,508,656 — Serfass et al shows a mixing pump which is feedback controlled from a conductivity cell.

Pumps having positive displacement cylinders with reciprocating pistons are driven by water pressure. U.S. Pat. Nos. 3,406,826 and 3,598,727 show dialysis systems having such pumps. These pumps have separate cylinders with an exposed piston rod connecting the cylinders. The exposed rod has seals which can leak creating build-up of salt encrustation. These pumps have valves which are driven by an exposed mechanical linkage between the reciprocating piston and the values. This exposes the operator to possible injury from the moving linkage parts. The mechanical linkage draws energy from the limited water pressure energy available for operation of the pump resulting in slower operation of the pump than would otherwise be possible. Also, the valve is slow to operate and causes a significant interruption of flow.

SUMMARY OF THE INVENTION

In accordance with this invention a reciprocating water driven pump is operated by proximity actuated switches connected to solenoid operated valves.

It is an object of the present invention to provide a completely enclosed pump with no external dynamic seals or moving parts.

It is a further object of the present invention to provide a proportioning pump in which siliconized glass cylinders offer a hard, precision, smooth, slippery bore and which are transparent for inspection of the interior of the pump.

In accordance with a particular embodiment of the invention, proximity operated switches are used to operate solenoid valves which make the proportioning components reciprocate. These switches sense the position of the proportioning piston, without physical contact, through the sealed pump enclosure. The electrically operated valve is fast operating and causes minimal disruption in the flow of fluid.

DESCRIPTION OF THE DRAWINGS

FIG. 1A shows the construction of the cylinder and pistons;

FIG. 2 is a perspective view of the pump; and

FIGS. 3 and 3A show the details of the pump seals.

DESCRIPTION OF A PARTICULAR EMBODIMENT

Figure 1:
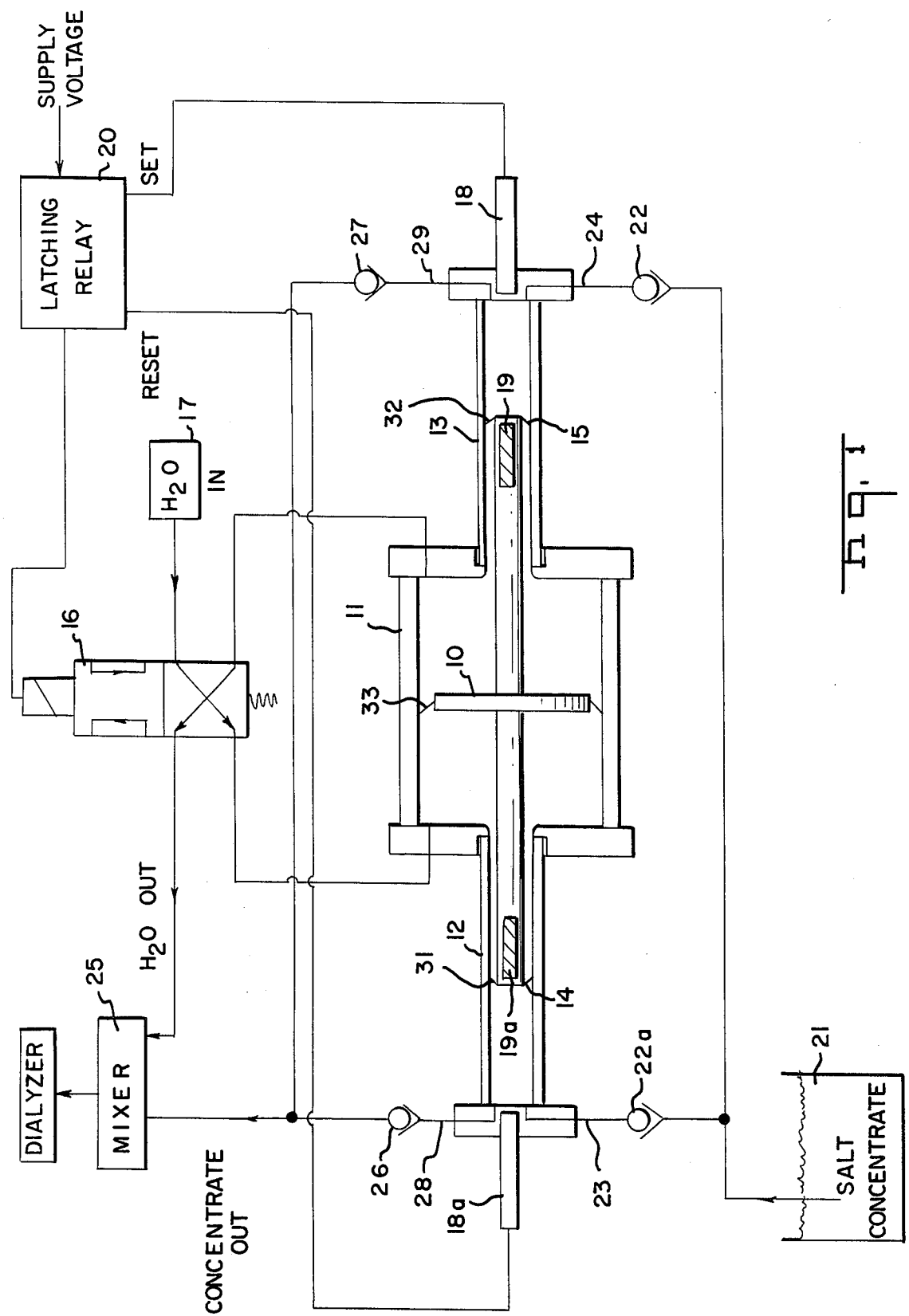
FIG. 1 shows the pump of this invention schematically.
Figure 7:
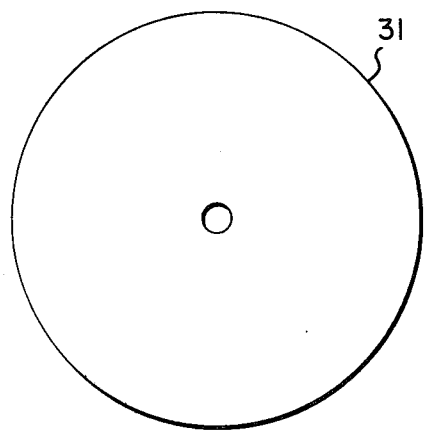
Figure 7A:
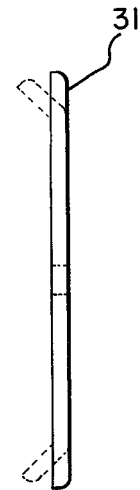

The pump for measuring predetermined quantities of liquid includes a double-acting center piston 10 enclosed within a center cylinder 11. End cylinders 12 and 13 are extensions of the center cylinder with no internal or external seals between cylinders and with no exposed moving parts between the cylinders. An end piston 14 is disposed within end cylinder 12 and an end piston 15 is disposed within end cylinder 13.

A bistable solenoid operated valve system 16 connects a source of liquid 17 to one side of the center cylinder 11. In the position shown, the valve connects the source of water under pressure to the left hand side of the center cylinder 11. The right hand side of the cylinder is connected through the valve 16 to its outlet. The valve system 16 is bistable and when it is in its other bistable state, the source of water 17 is connected to the right hand side of cylinder 11. In this position, the left hand side of cylinder 11 is connected through the valve 16 to the outlet.

Proximity actuated switches are enclosed in both ends of the end cylinders. As shown in FIG. 1, these include a magnetic switch 18 and a magnetic switch 18a. These switches are commonly referred to as reed switches and they are of the type which are magnetically operated. One commercially available switch which is suitable for use is Cat. No. RS—11—NO available from Alco Electronic Products, Inc., Andover, Massachusetts. A magnet 19 is disposed in the end piston 15 and it operates switch 18 when the piston 15 comes into close proximity thereto. Similarly, a magnetic 19a is in the end of piston 14. It actuates the switch 18a when it is in close proximity thereto.

A latching relay 20 is set by the switch 18 and it is reset by the switch 18a. This latching relay alternately energizes and de-energizes the solenoid operated valve 16 thus causing the pistion 10 to reciprocate.

The end cylinders 12 and 13 are used for the proportioning of concentrate. A source of concentrate 21 is connected through check valves 22 and 22a to the inlets 23 and 24 of end chambers 12 and 13 respectively.

A mixer 25 receives and combines the concentrate and the water. Check valves 26 and 27 are connected between the outlets 28 and 29 and the mixer 25.

As best seen in FIG. 2, the cylinders 11, 12 and 13 are precision bore glass cylinders. Such cylinders are available for example, from Fisher and Porter, Philadelphia, Pa. and from Corning Glass Works, Corning, N.Y. These cylinders are dipped in an aqueous silicate solution so that the inside surfaces are siliconized. One example of such a solution is SILICLAD TM available from Clay Adams, Parisppany, N.J. These glass cylinders economically provide a hard, precision smooth, slippery bore. The cylinders are particularly advantageously used in this type of pump because they make it possible to inspect the interior of the pump through the cylinders.

Each of the pistons has a cup type seal 31, 32 and 33 which provide the seal between each piston and its cylinder. FIGS. 3 and 3A show the details of the large seal before it is inserted in the cylinders. The seals are constructed of a durable rubber-like material. One material which is suitable for use is Rulon "J" supplied by the Dixon Corp., Bristol, R.I. When the seals on end pistons 14 and 15 are inserted, the seals are deformed into a cup toward the center cylinder. That is, the seal lip is bent toward the higher pressure which is present in the center cylinder 11. Note that there is concentrate on one side of the seal 31 and water pressure on the other side of seal 31. This pressure differential continuously expands the cup seal against the cylinder wall thereby minimizing the chances of leakage around the seal. The large center cup seal 33 is installed so that line pressure expands the cup against the cylinder when the electrical power is cut off and the piston travels to one end and stops. The piston always goes to its same end when the valve is de-energized.

While a particular embodiment of the invention has been shown and described, various modifications may be made without departing from the true spirit and scope of the invention. While the bistable valve system has been shown as including a latching relay, it is possible to use a true bistable valve without the need for a latching relay. There are a number of proximity sensing devices as photoelectric devices, capacitance sensing devices and others which are suitable for use. Other seals, valve configurations and cylinder materials can be used.

The appended claims are, therefore, intended to cover all such modifications.

What is claimed is:

1. A fluid pressure driven pump comprising:
    a double-acting piston means including a center cylinder, and a pair of end cylinders disposed on either side of said center cylinder, a center piston and end pistons each operated by said center piston, said end cylinders being extensions of said center cylinder with no exposed moving parts between said cylinders,
    switch means operated by said piston means,
    solenoid operated valve means alternately connecting opposite chambers of said center cylinder with a source of first fluid under pressure and an outlet of said valve means,
    valve means alternately connecting said end cylinders to a source of second fluid and to an outlet of said valve means, said switch means being connected to operate said solenoid operated valve means between alternate states as said piston means reciprocates within said cylinder,
    seals around the periphery of each end piston, said seals engaging said end cylinders to provide the only separation between said first fluid in said center cylinder and said second fluid in said end cylinders, and
    a cup seal around the periphery of said center cylinder, said cup seal being formed from a circular piece of compliant, durable rubber-like material which is deformed so that the outer periphery thereof bears against the inner surface of said center cylinder.

2. The pump recited in claim 1 wherein said switch means includes a magnetically actuated switch in the end of said end cylinder, and a permanent magnet on each end cylinder, said pump further including a latching relay which is set by one magnetic switch and reset by the other magnetic switch, said latching relay being connected to said solenoid operated valve means to operate it between said states.

3. The pump recited in claim 1 wherein both of said end cylinders have an inlet and an outlet,
    a check valve in each inlet and a check valve in each outlet,
    a source of second liquid connected through check valves to the inlets of both end cylinders, and
    means for receiving and combining said second liquid with the first named liquid, the outlets of said end cylinders being connected through check valves to said means, the outlet of said solenoid valve being connected to said means.

4. The pump recited in claim 1 further comprising a cup seal around the periphery of each end piston, the lip of the seal on each end piston being deformed toward the center cylinder.

5. The pump recited in claim 1 wherein said cylinders are precision bore siliconized glass cylinders.